United States Patent
Eichner et al.

(10) Patent No.: US 12,064,279 B2
(45) Date of Patent: Aug. 20, 2024

(54) DEVICE AND METHOD FOR EDITING A PANORAMIC RADIOGRAPHY IMAGE

(71) Applicant: DENTSPLY SIRONA INC., York, PA (US)

(72) Inventors: Stefan Eichner, Heidelberg (DE); Markus Hülsbusch, Bürstadt (DE)

(73) Assignee: DENTSPLY SIRONA INC., York, PA (US)

( * ) Notice: Subject to any disclaimer, the term of this patent is extended or adjusted under 35 U.S.C. 154(b) by 493 days.

(21) Appl. No.: 17/290,368

(22) PCT Filed: Nov. 7, 2019

(86) PCT No.: PCT/EP2019/080468
§ 371 (c)(1),
(2) Date: Apr. 30, 2021

(87) PCT Pub. No.: WO2020/094756
PCT Pub. Date: May 14, 2020

(65) Prior Publication Data
US 2021/0407159 A1 Dec. 30, 2021

(30) Foreign Application Priority Data
Nov. 7, 2018 (EP) .................................... 18204908

(51) Int. Cl.
*A61B 6/00* (2024.01)
*A61B 6/03* (2006.01)
(Continued)

(52) U.S. Cl.
CPC ............... *A61B 6/51* (2024.01); *A61B 6/032* (2013.01); *A61B 6/035* (2013.01); *A61B 6/4441* (2013.01);
(Continued)

(58) Field of Classification Search
CPC ........... A61B 6/032; A61B 6/035; A61B 6/14; A61B 6/44; A61B 6/4429; A61B 6/4435;
(Continued)

(56) References Cited

U.S. PATENT DOCUMENTS 5,214,686 A * 5/1993 Webber ................ A61B 6/4233
378/98.2
5,744,806 A * 4/1998 Fröjd ....................... A61B 6/51
378/19
(Continued)

FOREIGN PATENT DOCUMENTS

EP 2594201 A1 5/2013

OTHER PUBLICATIONS

International Search Report; PCT/EP2019/080468; Nov. 27, 2019 (completed); Dec. 6, 2019 (mailed).
(Continued)

*Primary Examiner* — Allen C. Ho
(74) *Attorney, Agent, or Firm* — DENTSPLY SIRONA INC.

(57) ABSTRACT

A device for editing a panoramic radiography image of an examination object generated by a panoramic X-ray machine, including: an input interface for receiving the panoramic radiography image as well as reconstruction data of the panoramic radiography image, the reconstruction data including information on a course of projection lines of the panoramic radiography image between an X-ray source and an X-ray detector of the panoramic X-ray machine as well as information on an image surface of the panoramic radiography image; an evaluation unit for evaluating the reconstruction data and for determining an image section of the panoramic radiography image that has been generated on the basis of one of the projection lines with two intersection points with the image surface; an image editing unit for
(Continued)

editing the panoramic radiography image based on the determined image section; and an output unit for outputting the edited panoramic radiography image.

12 Claims, 4 Drawing Sheets

(51) Int. Cl.
*A61B 6/46* (2024.01)
*A61B 6/50* (2024.01)
*A61B 6/51* (2024.01)
*G06T 11/00* (2006.01)
*G06T 11/60* (2006.01)

(52) U.S. Cl.
CPC .............. *A61B 6/461* (2013.01); *A61B 6/462* (2013.01); *A61B 6/463* (2013.01); *A61B 6/465* (2013.01); *A61B 6/467* (2013.01); *A61B 6/468* (2013.01); *A61B 6/469* (2013.01); *A61B 6/501* (2013.01); *A61B 6/5241* (2013.01); *A61B 6/5258* (2013.01); *G06T 11/008* (2013.01); *G06T 11/60* (2013.01); *G06T 2210/41* (2013.01)

(58) Field of Classification Search
CPC ... A61B 6/4441; A61B 6/4447; A61B 6/4476; A61B 6/4482; A61B 6/46; A61B 6/461; A61B 6/462; A61B 6/463; A61B 6/465; A61B 6/467; A61B 6/468; A61B 6/469; A61B 6/501; A61B 6/52; A61B 6/5205; A61B 6/5211; A61B 6/5241; A61B 6/5258

USPC ................................ 378/38–40, 62, 196–198
See application file for complete search history.

(56) References Cited

U.S. PATENT DOCUMENTS

| | | | | |
|---|---|---|---|---|
| 7,676,022 B2* | 3/2010 | Pantsar | ..................... | A61B 6/14 378/38 |
| 7,787,586 B2* | 8/2010 | Yoshimura | ............... | A61B 6/14 378/38 |
| 7,835,489 B2* | 11/2010 | Borghese | ............... | G16H 30/20 378/38 |
| 8,817,944 B2* | 8/2014 | Arai | ..................... | A61B 6/4452 378/11 |
| 9,036,881 B2* | 5/2015 | Carlson | .................... | A61B 6/14 382/131 |
| 9,113,799 B2* | 8/2015 | Katsumata | ........... | A61B 6/5258 |
| 9,427,197 B2* | 8/2016 | Zoccatelli | ................ | A61B 6/03 |
| 9,532,755 B2* | 1/2017 | Choi | ..................... | A61B 6/582 |
| 9,668,705 B2* | 6/2017 | Yamakawa | ........... | A61B 6/466 |
| 9,684,952 B2* | 6/2017 | Carlson | ............... | A61B 6/4435 |
| 9,993,212 B2* | 6/2018 | Takemoto | .............. | A61B 6/032 |
| 10,049,467 B2* | 8/2018 | Im | ......................... | G06T 11/005 |
| 10,346,957 B2* | 7/2019 | Ulrici | ........................ | G06T 7/30 |
| 10,813,605 B2* | 10/2020 | Arai | ......................... | A61B 6/54 |
| 2009/0323891 A1 | 12/2009 | Borghese | | |
| 2015/0254816 A1 | 9/2015 | Carlson | | |

OTHER PUBLICATIONS

Written Opinion of the International Searching Authority; PCT/EP2019/080468; Nov. 27, 2019 (completed); Dec. 6, 2019 (mailed).
International Preliminary Report on Patentability; PCT/EP2019/080468; Nov. 27, 2019 (completed); Dec. 6, 2019 (mailed).

* cited by examiner

DEVICE AND METHOD FOR EDITING A PANORAMIC RADIOGRAPHY IMAGE

CROSS-REFERENCE TO RELATED APPLICATIONS

This is a National Phase application of International Application No. PCT/EP2019/080468 filed Nov. 7, 2019, which claims the benefit of and priority to European Patent Application Number EP18204908.0A filed on Nov. 7, 2018 which are herein incorporated by reference for all purposes.

TECHNICAL FIELD

The present invention relates to a device and a method for editing a panoramic radiography image of an examination object generated by a panoramic X-ray machine. Moreover, the invention relates to a diagnosis system for examining a craniomaxillofacial area of a patient.

BACKGROUND OF THE INVENTION

X-ray examinations have been a widely-used standard procedure for many years particularly in medicine but also in industry as well as in other fields of application. X-rays are absorbed differently in structures with various thicknesses within an examination object so that an image of an inner structure can be generated. In medical diagnostics, the inside of a human body can thus be examined.

In this respect, single X-ray images can be generated, several images taken from different angles can be composed to a panoramic image (panoramic X-ray machine) or three-dimensional models can be reconstructed from spatially different projections (X-ray tomography or X-ray computed tomography). The various methods differ particularly in the level of radiation that the examination object is exposed to.

In odontology, images of single teeth, groups of teeth or of the whole jaw are particularly common. As X-ray radiation penetrates the human head during the examination, the used level of radiation is of high relevance. Almost all dental surgeries have X-ray machines but different machines are used or different images are generated depending on the type of examination carried out.

Extraoral panoramic X-ray machines, i.e. machines without an X-ray source and/or an X-ray receiver in the patient's mouth, travel around the head and the jaw of a patient. For this purpose, an X-ray source is usually attached to one side of an arm and an X-ray detector to the other. To generate a sharp image within the area of interest in the patient's jaw, specific machine trajectories are used to travel around the head. A machine trajectory thereby defines an image surface of a panoramic radiography image as that surface, within the object that is penetrated by x-ray radiation from several angles, that is reproduced as a sharp image (focused).

A challenge in the use of panoramic radiography images is the presence of image artifacts. In particular when a panoramic radiography image of a human jaw arch is generated, radiation passes, in some areas of the trajectory, through the jaw of interest as well as through the opposing jaw on the opposite side. This may result in structures of the opposing jaw superimposing structures of the jaw of interest as artifacts in the image. This makes a diagnosis more difficult. Even if only a hemifacial image is taken, i.e. an image of half the jaw, such opposing jaw artifacts (for example bright shadows or stripes) are visible. Metallic foreign objects or other objects on the patient may result in further unexpected and possibly disturbing opposing jaw artifacts.

To solve this problem, the machine trajectory (may also be called trajectory curve) can be adjusted. So-called artifact-reduced trajectory curves have the effect that unavoidable opposing jaw artifacts are moved to other image sections that are diagnostically irrelevant. However, this approach requires deviating from an ideal radiography direction of the jaw arch, which may possibly increase the level of radiation exposure and/or decrease image quality. A further approach is the use of three-dimensional methods. In this connection, DE 10 2010 040 096 A1 describes a method for generating an image from a 3D volume. A virtual dental image is generated from a 3D volume with volumetric image data. At first, a part volume of the 3D volume is defined and then a virtual projection image from a certain radiography direction is generated for this part volume by computer-aided calculation of the volumetric image data in this radiography direction. A calculation of a simulated panoramic radiography image without involvement of the opposing jaw is thus made possible. However, the level of radiation exposure of a 3D image is higher and the resolution is worse.

US 2009/323891 A1 discloses a method and apparatus for simplified patient positioning in dental tomographic x-ray imaging.

EP2594201 A1 discloses a panoramic dental X-ray unit.

US 2015/254816 A1 discloses alignment of mixed-modality data sets for reduction and removal of imaging artifacts.

SUMMARY OF THE INVENTION

On this basis, the present invention addresses the problem of improving diagnoses based on panoramic radiography images. The level of radiation exposure shall be kept at a minimum. In particular, a possibility for examining a human jaw arch shall be achieved.

For solving this problem, an aspect of the present invention relates to a device for editing a panoramic radiography image of an examination object generated by a panoramic X-ray machine, comprising: an input interface for receiving the panoramic radiography image as well as reconstruction data of the panoramic radiography image, the reconstruction data including information on a course of projection lines of the panoramic radiography image between an X-ray source and an X-ray detector of the panoramic X-ray machine as well as information on an image surface of the panoramic radiography image; an evaluation unit for evaluating the reconstruction data and for determining, on the basis of one of the projection lines with two intersection points with the image surface, an image section of the panoramic radiography image that has been generated; an image editing unit for editing the panoramic radiography image based on the determined image section; and an output unit for outputting the edited panoramic radiography image.

A further aspect of the present invention relates to a diagnosis system for examining a craniomaxillofacial area of a patient, comprising: an extraoral panoramic dental X-ray machine with an X-ray source that is movable around a patient's head and with an X-ray detector that is fixedly connected with the X-ray source; and a device as described above.

Further aspects of the invention relate to a method configured according to the device described above as well as to a computer program product with program code for executing the steps of the method when the program code is executed on a computer, as well as a storage medium on which a computer program is stored, which, when executed on a computer, effects an execution of the method described herein.

Preferred embodiments of the invention are described in the dependent claims. It is understood that the features mentioned hereinbefore and those to be commented on hereinafter may be used not only in the specified combination but also in other combinations or in isolation without departing from the scope of the present invention. In particular, the method and the computer program product may be configured in accordance with the embodiments of the device and the diagnosis system described in the dependent claims.

According to the invention, it is provided that, on the one hand, a panoramic radiography image and, on the other hand, the reconstruction data of the panoramic radiography image are received. The panoramic radiography image in particular corresponds to respective image data. The reconstruction data in particular comprise geometric information on the machine trajectory of the panoramic X-ray machine as well as on the geometric arrangement of the radiator, screen, and detector and of the examination object (radiation geometry) as well as the resulting focus and/or image surface, in which a sharp image has been generated. Additionally, the reconstruction data preferably comprise information on the geometry on the basis of which an overall image has been generated from several recorded X-ray images.

On the basis of the reconstruction data, an image section within the panoramic radiography image may be determined, which potentially includes artifacts, in particular opposing jaw artifacts. This image section corresponds to a section that has been generated on the basis of at least one projection line that crosses the image surface twice. To determine the respective image section, the image surface as well as the course of the projection lines relative to the image surface has to be known. According to the invention, the determined image section is edited. Thus, a section of the panoramic radiography image is edited in which there may possibly be an artifact. The panoramic radiography image with the edited image section is output via the output unit.

In comparison with known approaches of displaying panoramic radiography images, according to the invention, an image section is edited before the image is output. Editing may occur before, during or after an evaluation. In particular, editing may occur prior to a diagnosis based on the image. It is not necessary to increase the level of radiation exposure. No additional image is generated but an already generated image is edited. The accuracy of the diagnosis is improved. Impairment of the evaluation of a panoramic radiography image because of artifacts is avoided or reduced respectively.

In a preferred embodiment, the input interface is configured to receive the panoramic radiography image as well as the reconstruction data from an extraoral panoramic dental X-ray machine. Preferably, the device according to the invention is used in the field of dental diagnostics. Opposing jaw artifacts and/or respective image sections can be recognized. The accuracy of the diagnosis is increased. Qualified medical staff may evaluate panoramic radiography images of a human jaw without unidentified opposing jaw artifacts causing inaccuracies.

In a further advantageous embodiment, the reconstruction data comprise a relative position of the image surface in relation to the projection lines and/or a description of a movement of a movable X-ray source in relation to the examination object. It is particularly advantageous if the relative position of the image surface is described for instance by geometric information and/or a description by means of a coordinate system. Respective geometric information may also be used for the description of the movement of the X-ray source. Such reconstruction data allow for an efficient evaluation and a reliable determination of the image section of the panoramic radiography image that potentially includes artifacts. Preferably, the X-ray source is fixedly connected with an X-ray detector that is also moveable.

In a further advantageous embodiment, the image editing unit is configured to mark a section and/or a spot in the panoramic radiography image. The mark preferably comprises a color tag and/or a frame. Advantageously, the section within the panoramic radiography image that potentially includes artifacts is marked. For this purpose, a respective frame (circle, rectangle, etc.) or a color tag (for example yellow shadow etc.) may be used. By marking the relevant section of the image, it is indicated that any possible artifacts should be paid attention to when the image is evaluated within this section or at this spot respectively. In this respect, marking serves to simplify evaluation.

In an advantageous embodiment, the evaluation unit is configured to determine a multi-part, in particular a two-part, image section that corresponds to all projection lines with two intersection points with the image surface. In particular, it is possible to fully mark the section that potentially includes artifacts. Advantageously, the image section is correspondingly marked twice, i.e. on both sides of a panoramic radiography image. When a panoramic radiography image thus edited is evaluated, it is hereby defined in which sections artifacts may possibly exist.

In an advantageous embodiment, the image editing unit is configured to subtract an image value of a first intersection point, preferably close to the X-ray source, of a projection line with the image surface from an image value of a second intersection point of the projection line with the image surface. Editing may in particular comprise a step of subtracting an image value. Subtracting an image value may compensate for artifacts. For example, a weighting may be carried out. This further increases the accuracy of the diagnosis.

Advantageously, the input interface is configured to receive a marking position, which corresponds to a first intersection point of a first projection line with the image surface. Further, the evaluation unit is configured to determine an image section, which corresponds to a second intersection point of the first projection line with the image surface. A marking position may additionally be received via the input interface. On this basis, a corresponding image section on an opposite side is then determined. By simultaneously viewing the marking position as well as the determined opposite section an impression can be obtained as to the possible structures in this opposite section that represent the source of a possible artifact. On this basis, an improved diagnosis is made possible as it can be checked immediately if an object in the section of the marking position may possibly be traced back to an artifact. The diagnosis is further simplified. The reliability is increased.

In an advantageous embodiment, the device comprises a user interface for entering the marking position by a user of the device. Preferably, the marking position may be entered by choosing a position on a representation of the panoramic radiography image by means of a touch screen, touch pad, touch pen, and/or a computer mouse. It is made possible that a user, for example a member of the evaluating qualified medical staff, makes an entry and it is directly displayed for this entry if and where there is an opposite image section from which possible artifacts may originate. It is thus achieved that in case of a noticeable object in the panoramic radiography image, it can be clarified directly and interactively if this noticeable object was caused by an artifact on the opposite side.

In an embodiment, the output unit is configured to output the edited panoramic radiography image on a display. Preferably, a computer-based output is possible. This allows for interaction with the user. Moreover, functions of computer-aided display, such as magnifications etc., may be used.

In a further advantageous embodiment of the diagnosis system, the panoramic dental X-ray machine is configured to generate the panoramic radiography image from a composition of a plurality of single images. The single images are generated at different positions of the X-ray source and the X-ray detector relative to the examination object. It is particularly advantageous to use data of a panoramic dental X-ray machine that has recorded and composed several single images. The accuracy of the diagnosis may be increased.

Herein, an examination object may be any organic or inorganic object. In particular, a body part of a human being may be examined. Preferably, a jaw area of a human being is examined as examination object. The panoramic radiography image may in particular be available in the form of digital image data. A course of projection lines may in particular follow geometric specifications within a coordinate system in the panoramic X-ray machine. A projection line corresponds to an imagined line between X-ray source and X-ray detector. In particular, projection lines are herein understood as rays that fan out across the distance. A projection fan or projection cone advantageously comprises several projection lines. In particular, a course of projection lines may comprise and/or represent a geometric description of a fan or a cone. Correspondingly, an intersection point may herein also feature a spatial dilation and insofar correspond to an intersection area. The editing of the panoramic radiography image according to the invention may comprise an editing of single pixels or image values. A craniomaxillofacial area of a patient in particular describes the area of the jaw and/or the jaw arch of a patient (dental area).

BRIEF DESCRIPTION OF THE DRAWINGS

The invention is described and explained in more detail by means of a number of selected embodiments in connection with the enclosed Figures hereinafter. In the Figures.

DETAILED DESCRIPTION OF THE INVENTION

Figure 1:
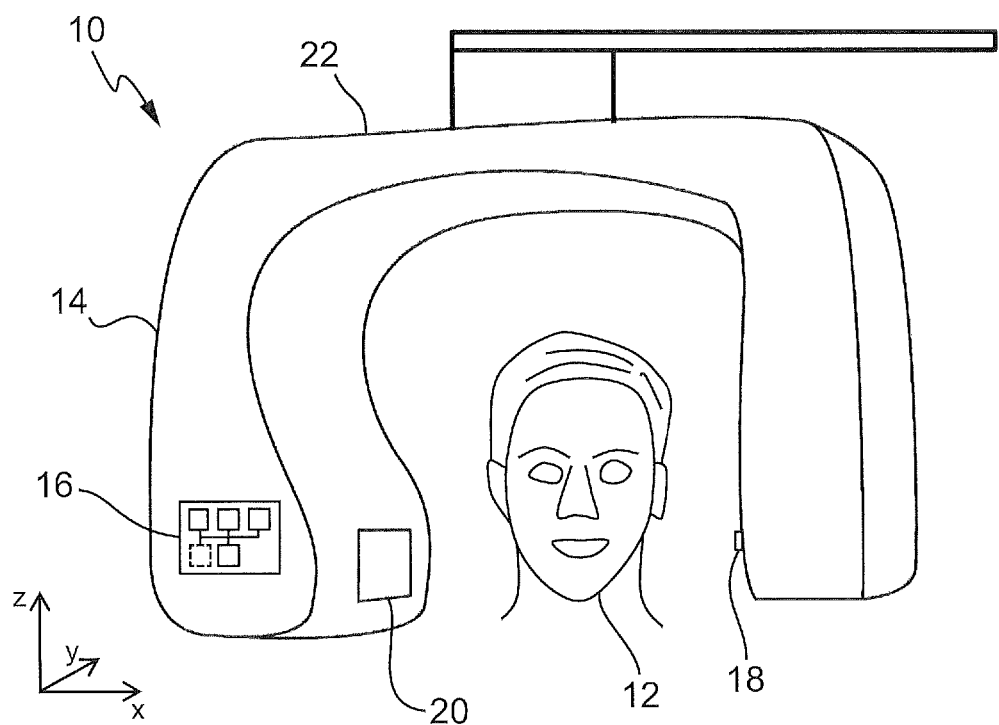
FIG. 1 shows a schematic illustration of a diagnosis system according to the invention for examining a craniomaxillofacial area of a patient.

FIG. 1 illustrates a diagnosis system 10 according to the invention for examining a craniomaxillofacial area of a patient. The diagnosis system 10 comprises a panoramic X-ray machine 14 as well as a device 16 for editing a panoramic radiography image generated by a panoramic X-ray machine 14. In particular, a panoramic X-ray machine 14 for use in dental diagnostics is shown (panoramic dental X-ray machine).

In the exemplary illustrated embodiment, the head of the patient is examined as examination object 12. An X-ray source 18 that is movable around the examination object 12 emits X-ray radiation that penetrates the examination object 12 and is received by an X-ray detector 20. X-ray source 18 and X-ray detector 20 are fixedly connected via a respective rotatable arc 22 (may also be referred to as arm). Usually, the arc 22 is revolvably or rotatably mounted at a position above the examination object 12. X-ray source 18 and X-ray detector 20 travel around the examination object 12 along a machine trajectory. This machine trajectory does not have to correspond to a circular trajectory. In the exemplary illustrated embodiment, the device 16 is integrated in the panoramic X-ray machine 14. It is also possible that the device 16 is arranged elsewhere. For instance, the device 16 may be fully or partly integrated in a separate evaluation computer. The device 16 may be fully or partly implemented in software. It is also possible that the device is implemented as a cloud service.

Figure 2:
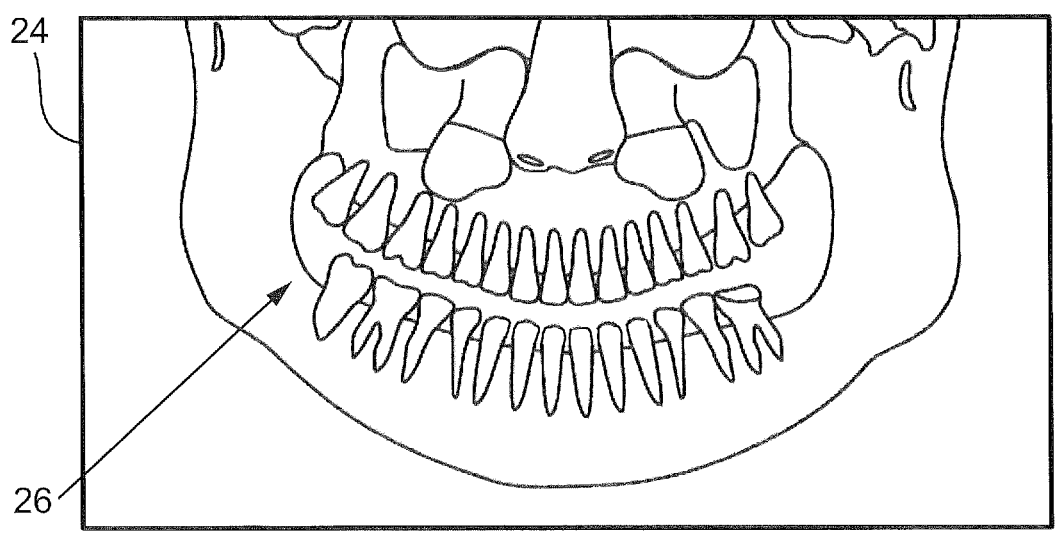
FIG. 2 shows a schematic illustration of a panoramic X-ray image without a complete representation of the temporomandibular joint.

FIG. 2 shows an exemplary panoramic radiography image of the jaw arch 26 of a patient that can be generated by means of a panoramic X-ray machine. In the exemplary illustrated embodiment, the panoramic radiography image 24 corresponds to a composition of a plurality of single images that have been recorded during a movement of the X-ray source and the connected X-ray detector around the examination object.

Figure 3:
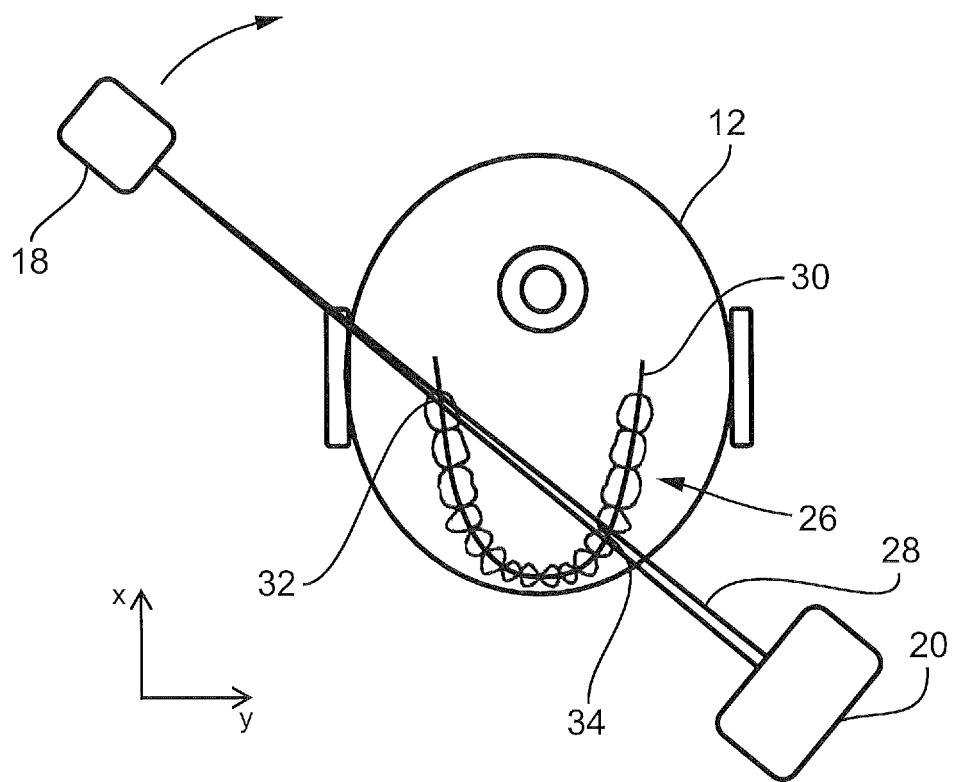
FIG. 3 shows a schematic illustration of a top view of an examination object in a diagnosis system according to the invention.

In FIG. 3, the movement of the X-ray detector 20 and the X-ray source 18 around the examination object 12 or the patient's head, respectively, is shown.

The view corresponds to a top view from a bird's eye view. In particular, a cross-section in a plane perpendicular to the z-axis (cf. FIG. 1) is shown.

As illustrated, a projection line 28 runs from the X-ray source 18 to the X-ray detector 20. The projection line 28 corresponds to an imagined line, wherein the projection or ray geometry may also be based on a fanning out and a respective projection fan or projection cone. A projection fan or a projection cone respectively are herein regarded as several projection lines 28.

The movement of the X-ray source 18 and the X-ray detector 20 during generation of the panoramic radiography image 24 usually occurs along a predetermined machine trajectory that, in most cases, does not correspond to a circular trajectory. To generate a sharp image of the jaw arch 26, it is necessary for an image surface 30 to be within the area of the jaw arch 26 as much as possible. The image surface 30 corresponds to a surface that has been determined on the basis of the ray geometry, the trajectory curve, and the reconstruction to generate a sharp image of the jaw arch 26.

As illustrated schematically, there are sections in which the projection line 28 intersects the image surface 30 twice, thus comprising a first intersection point 32 in the vicinity of the X-ray source 18 as well as a second intersection point 34 averted from the X-ray source 18. The image surface 30 mostly lies on the side of the second intersection point 34 that is averted from the X-ray source 18 (in the vicinity of the sensor or detector). Due to the fact that the projection line 28 intersects the image surface 30 once in the first intersection point 32 before it reaches the second intersection point 34 or the X-ray detector 20 respectively, there are overlays in the image section of the panoramic radiography image 24, which corresponds to the second intersection point 34 of the projection line 28. In the field of dental X-ray technology, the resulting artifacts are described as opposing jaw artifacts.

Figure 4:
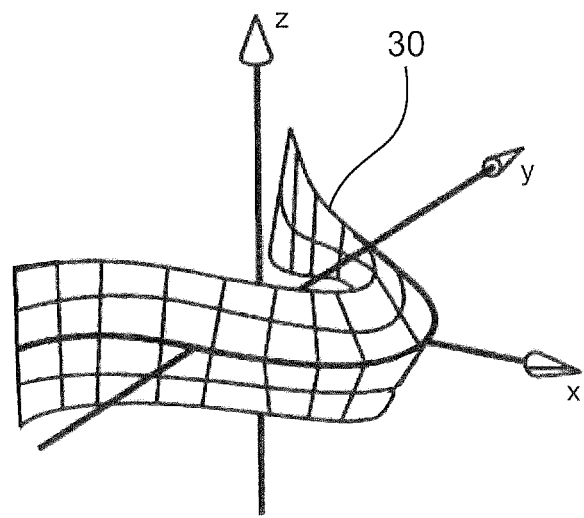
FIG. 4 shows a schematic illustration of an image surface.

FIG. 4 illustrates a schematic illustration of an image surface 30 in a spatial representation. The distance of the image surface 30 to the X-ray source 18 and/or the X-ray detector 20, from which distance a sharp panoramic image results, is mostly not constant while the panoramic image is being generated. In other words, the image points or the image surface 30, respectively, are defined by the position of X-ray source 18 and X-ray detector 20. The initial characteristics of the image surface 30 with respect to position, form, and course in particular results from the movement of the X-ray source 18 and the X-ray detector 20 around the examination object 12 along the machine trajectory. Thus, on the one hand, the image surface 30 depends on the geometry of the panoramic dental X-ray machine as well as, on the other hand, on the chosen ray geometry and reconstruction specific to the trajectory (reconstruction data). To describe the reconstruction, a geometric description of the movement of the X-ray source 18 in relation to the examination object 12 and/or a description of the image surface 30 by means of geometric data may particularly be used. In most cases, it is possible to predetermine a machine trajectory of a panoramic dental X-ray machine within certain parameters and to thus influence and/or define the characteristics of the image surface 30. For example, a different machine trajectory can be used for a child than for an adult so as to reach, based on a fixed position of the patient's head in relation to the X-ray machine, a circulation of the X-ray source 18 and the X-ray detector 20 that is as customized as possible.

Figure 5:
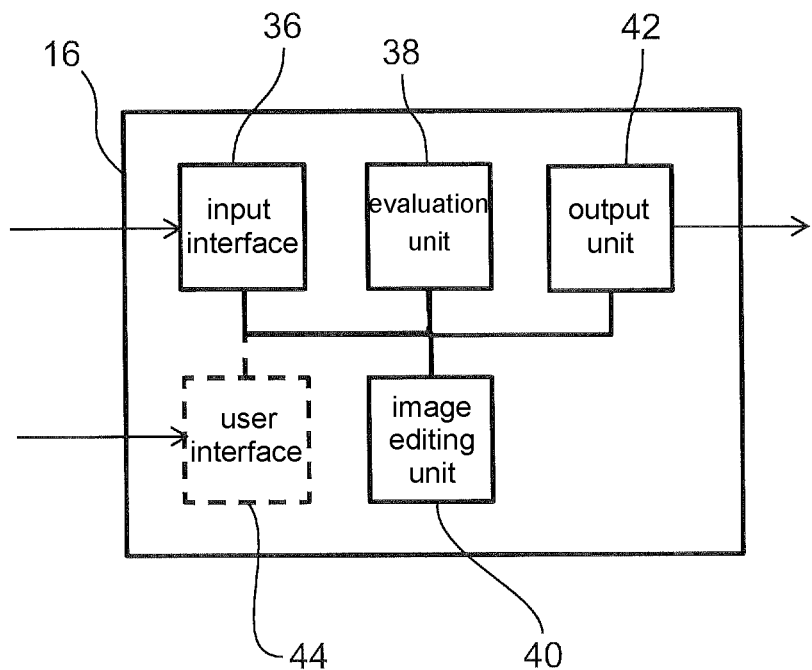
FIG. 5 shows a schematic illustration of a device according to the invention.
Figure 6:
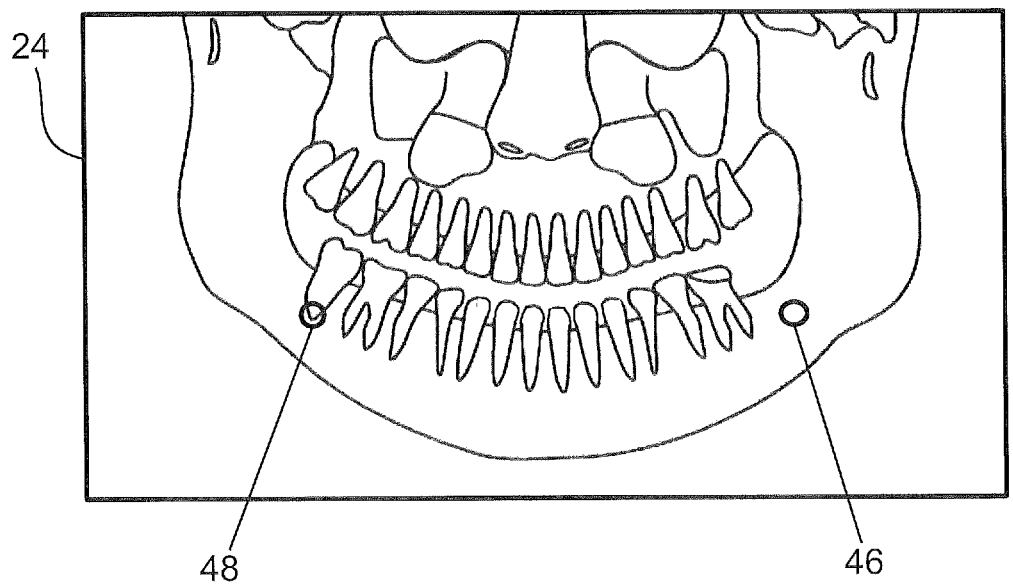
FIG. 6 shows a schematic illustration of a panoramic radiography image according to the invention.
Figure 7:
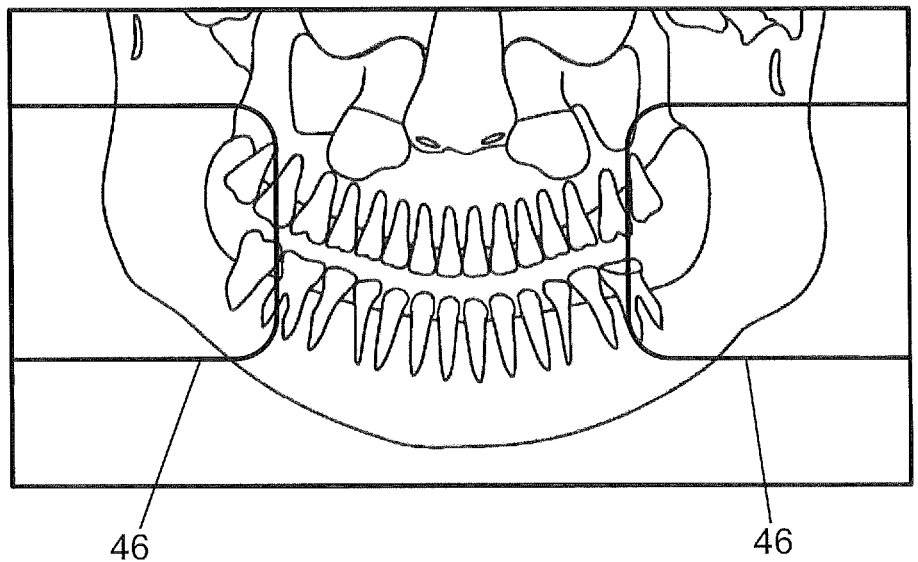
FIG. 7 shows a schematic illustration of a further panoramic radiography image according to the invention.

FIG. 5 schematically illustrates a device 16 according to the invention. The device 16 comprises an input interface 36, an evaluation unit 38, an image editing unit 40 as well as an output unit 42. Optionally, the device 16 according to the invention also comprises a user interface 44. The different units may particularly be configured as a processor, a processor module or as software for a processor. The device 16 according to the invention may partly or completely be implemented in software and/or hardware. For instance, the device 16 may be integrated in an X-ray machine or may be implemented in an evaluation computer in the form of software.

Via the input interface 36, a panoramic radiography image 24 as well as reconstruction data of the panoramic radiography image 24 are received. The input interface 36 may for instance be implemented in hardware as a plug connection. But it is also possible that the input interface 36 is configured as a respective software interface for receiving data. The panoramic radiography image 24 itself preferably comprises the digital image data (pixel values and/or image values) that have been generated by a respective panoramic X-ray machine 14. In particular, image data are received after the panoramic radiography image 24 has been reconstructed on the basis of several single images. Insofar, data processing of the device 16 according to the invention and/or the diagnosis system 10 according to the invention is based on X-ray data that have been obtained using a (digital) panoramic sensor.

In addition to the actual image data of the panoramic radiography image 24, the input interface 36 is configured to receive reconstruction data. The reconstruction data comprise information on a course of projection lines as well as information on an image surface 30. In particular, it is possible that reconstruction data with a geometric description of the course of the projection lines as well as the image surface 30 are received. The geometric description may for example be received in a Euclidean or other coordinate system or in other manners.

The received reconstruction data are evaluated in the evaluation unit 38 in order to identify an image section of the panoramic radiography image 24 that has been generated on the basis of a projection line 28 with two intersection points with the image surface 30. In other words, based on the position of the image plane, it is calculated which image sections of the panoramic radiography image 24 may possibly be affected by artifacts due to a double intersection point of the projection lines with the image surface 30. Different mathematical-geometric methods may be used for this purpose. In particular, it is possible that an approximate consideration is used for more complex geometries of an image surface 30.

In the image editing unit 40, the determined section within the image is edited. In particular, editing is understood to mean an adjustment of the gray and/or color values of the single pixels. For instance, the determined image section can be marked by adding a color to each pixel value. It is also possible to generate a frame around the determined section or to carry out editing in another form.

It is particularly advantageous if a complete or partial compensation of artifacts is carried out. For this purpose, an image value of a second intersection point 34 of a projection line 28 with the image surface 30 may be subtracted from an image value of a first intersection point 32 of the projection line with the image surface 30. In other words, a reprojection of the panoramic image onto itself may be carried out. Thereby, artifacts are reduced as at least a partial compensation is generated within the image.

The output unit 42 is configured to output the edited panoramic radiography image 24. In particular, the output unit 42 may be directly connected to a respective display device, e.g. a (touch screen) display, on which the edited panoramic radiography image 24 is displayed. For example, a display may be connected in a dental surgery.

Via the optional user interface 44, it is possible for a user, for instance a dentist or a member of the qualified medical staff, to define a position (marking position); in the evaluation unit 38, an image section is then automatically identified that corresponds to a related opposite and/or second intersection point 34 of a projection line 28 that has a first intersection point 32 with the image surface 30 at the marking position. It is thus, for example, made possible to mark or click an image section by means of a computer mouse or a touch screen and to then directly visualize from which section corresponding artifacts may originate. Insofar, it can be clarified interactively if a non-attributable object within the image might possibly correspond to an artifact.

Figure 8:
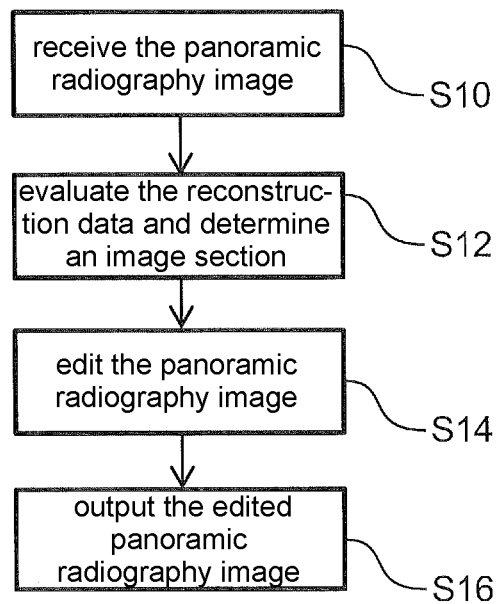
FIG. 8 shows a schematic illustration of a method according to the invention.

FIG. 8 schematically shows a method according to the invention. The method comprises steps of receiving S10 the panoramic radiography image, of evaluating S12 the reconstruction data and determining an image section, of editing S14 the panoramic radiography image and of outputting S16 the edited panoramic radiography image. The method according to the invention may for example be implemented as software for a diagnosis system or also as stand-alone software.

In the Figures, a use of the invention in the field of odontology was particularly addressed. It is understood that a use in other fields, for example within medicine or industrial radiography, is also possible.

The invention was comprehensively described and explained by means of the Figures and the description. The description and explanations are to be regarded as examples and not as limiting the scope. The invention is not limited to the disclosed embodiments. For the person skilled in the art, other embodiments or variants follow from the use of the present invention as well as from a thorough analysis of the Figures, the description and the following patent claims.

In the patent claims, the words "comprise" and "include" do not exclude the presence of further elements or steps. The indefinite article "a" or "an" does not exclude the presence of a plural. A single element or a single unit may execute the functions of several of the units named in the patent claims. An element, a unit, a device and a system may, partly or entirely, be implemented in hardware and/or software. The mere mention of some measures in several different dependent patent claims is not to be understood to the effect that a combination of these measures cannot also be used advantageously. A computer program may be stored/distributed on a non-volatile data carrier, for example on an optical memory device or on a solid state drive (SSD). A computer program may be distributed together with hardware and/or as part of hardware, for example on the Internet or via wire-bound or wireless communication systems. Reference signs in the patent claims are not to be understood as limiting the scope of the invention.

The invention claimed is:

1. A device for editing a panoramic radiography image of an examination object generated by a panoramic X-ray machine, comprising:
    an input interface for receiving the panoramic radiography image as well as reconstruction data of the panoramic radiography image, the reconstruction data including information on a course of projection lines of the panoramic radiography image between an X-ray source and an X-ray detector of the panoramic X-ray machine as well as information on an image surface of the panoramic radiography image;
    an evaluation unit for evaluating the reconstruction data and for determining, on a basis of one of the projection lines with two intersection points with the image surface, an image section of the panoramic radiography image that has been generated;
    an image editing unit for editing the panoramic radiography image based on the determined image section; and
    an output unit for outputting the edited panoramic radiography image.

2. The device according to claim 1, wherein the input interface is configured to receive the panoramic radiography image as well as the reconstruction data from an extraoral panoramic dental X-ray machine.

3. The device according to claim 1, wherein the reconstruction data of the panoramic radiography image comprise a relative position of the image surface of the panoramic radiography image in relation to the projection lines and/or a description of a movement of the X-ray source in relation to the examination object.

4. The device according to claim 1, wherein the image editing unit is configured to mark a section and/or a spot in the panoramic radiography image to obtain a mark; and
    the mark comprises a color tag and/or a frame.

5. The device according to claim 1, wherein the evaluation unit is configured to determine a two-part image section that corresponds to all projection lines with two intersection points with the image surface.

6. The device according to claim 1, wherein the image editing unit is configured to subtract an image value of a first intersection point, close to the X-ray source, of a projection line with the image surface from an image value of a second intersection point of the projection line with the image surface.

7. The device according to claim 1, wherein
    the input interface is configured to receive a first marking position, which corresponds to a first intersection point of a first projection line with the image surface; and
    the evaluation unit is configured to determine an image section, which corresponds to a second intersection point of the first projection line with the image surface.

8. The device according to claim 1, wherein the output unit is configured to output the edited panoramic radiography image on a display.

9. A diagnosis system for examining a craniomaxillofacial area of a patient, comprising:
    an extraoral panoramic dental X-ray machine comprising an X-ray source that is movable around a patient's head and an X-ray detector that is fixedly connected with the X-ray source; and
    a device according to claim 1.

10. The diagnosis system according to claim 9, wherein the extraoral panoramic dental X-ray machine is configured to generate a panoramic radiography image from a composition of a plurality of single images that have been generated at different positions of the X-ray source and the X-ray detector relative to the examination object.

11. A method for editing a panoramic radiography image of an examination object generated by a panoramic X-ray machine, comprising the steps of:
    receiving the panoramic radiography image as well as reconstruction data of the panoramic radiography image, the reconstruction data including information on a course of projection lines of the panoramic radiography image between an X-ray source and an X-ray detector of the panoramic X-ray machine as well as information on an image surface of the panoramic radiography image;
    evaluating the reconstruction data and determining, on a basis of one of the projection lines with two intersection points with the image surface, an image section of the panoramic radiography image that has been generated;
    editing the panoramic radiography image based on the determined image section; and
    outputting the edited panoramic radiography image.

12. A non-transitory computer-readable storage medium, including instructions that when executed by a computer, cause the computer to:
    receive a panoramic radiography image of an examination object generated by a panoramic X-ray machine, as well as reconstruction data of the panoramic radiography image, the reconstruction data including information on a course of projection lines of the panoramic radiography image between an X-ray source and an X-ray detector of the panoramic X-ray machine as well as information on an image surface of the panoramic radiography image;
evaluate the reconstruction data and determining, on a basis of one of the projection lines with two intersection points with the image surface, an image section of the panoramic radiography image that has been generated;
edit the panoramic radiography image based on the determined image section; and
output the edited panoramic radiography image.

* * * * *